United States Patent
Arregui San Martin et al.

(10) Patent No.: US 11,009,501 B2
(45) Date of Patent: May 18, 2021

(54) DEVICE FOR MEASURING THE CONCENTRATION OF GASES IN EXHALED AIR AND MEASUREMENT PROCEDURE USED

(71) Applicant: EVERSENS, S.L., Pamplona (ES)

(72) Inventors: Francisco Javier Arregui San Martin, Pamplona (ES); Miguel Angel Arangoa Ortega, Pamplona (ES); Leyre Ruete Ibarrola, Pamplona (ES); Ignacio Raul Matias Maestro, Pamplona (ES); Juan Maria Perez Azpeitia, Pamplona (ES)

(73) Assignee: EVERSENS, S.L., Pamplona (ES)

( * ) Notice: Subject to any disclaimer, the term of this patent is extended or adjusted under 35 U.S.C. 154(b) by 374 days.

(21) Appl. No.: 16/304,504

(22) PCT Filed: May 17, 2017

(86) PCT No.: PCT/ES2017/070327
§ 371 (c)(1),
(2) Date: Nov. 26, 2018

(87) PCT Pub. No.: WO2017/203075
PCT Pub. Date: Nov. 30, 2017

(65) Prior Publication Data
US 2019/0137480 A1     May 9, 2019

(30) Foreign Application Priority Data

May 27, 2016   (ES) ................. ES201630690

(51) Int. Cl.
*G01N 33/497*   (2006.01)
*A61B 5/08*     (2006.01)
(Continued)

(52) U.S. Cl.
CPC .......... *G01N 33/497* (2013.01); *A61B 5/082* (2013.01); *A61B 5/087* (2013.01); *A61B 5/097* (2013.01);
(Continued)

(58) Field of Classification Search
CPC ............. G01N 33/497; G01N 33/0037; G01N 2033/4975; A61B 5/08; A61B 5/082;
(Continued)

(56) References Cited

U.S. PATENT DOCUMENTS

2003/0050567 A1* 3/2003 Baghdassarian ....... A61B 5/097
600/532
2014/0228699 A1* 8/2014 Causevic ............... A61B 5/087
600/532
(Continued)

FOREIGN PATENT DOCUMENTS

EP    3000392 A1 *  3/2016 ............ A61B 5/087
ES    2221596 T3     7/2004
(Continued)

OTHER PUBLICATIONS

EP-3000392-A1-English (Year: 2016).*
(Continued)

*Primary Examiner* — Peter J Macciarolo
*Assistant Examiner* — Fatemeh Esfandiari Nia
(74) *Attorney, Agent, or Firm* — Lucas & Mercanti, LLP

(57) ABSTRACT

Device for measuring the concentration of gases in exhaled air and measurement procedure used, such device comprising a first air inlet (1), a second air inlet (3) with a nitric oxide filter (4), a pump (5), a nitric oxide sensor (6), a first valve (8) located downstream from the first air inlet (1) and upstream from the sensor (6), a second valve (9) located downstream from the second air inlet (3) and upstream from the sensor (6), a third valve (10) located downstream from
(Continued)

the sensor (6) in a first fluid line that conducts air to a first air outlet (12), and a fourth valve (11) located downstream from the sensor (6) in a second fluid line that conducts air to a second air outlet (13), wherein the pump (5) is located in the second fluid line.

13 Claims, 3 Drawing Sheets

(51) Int. Cl.
    *A61B 5/087*     (2006.01)
    *A61B 5/097*     (2006.01)
    *G01N 33/00*     (2006.01)

(52) U.S. Cl.
    CPC .. *G01N 33/0037* (2013.01); *A61B 2560/0247* (2013.01); *A61B 2562/0247* (2013.01); *G01N 2033/4975* (2013.01)

(58) Field of Classification Search
    CPC . A61B 5/087; A61B 5/097; A61B 2560/0247; A61B 2562/0247; Y02A 50/20
    See application file for complete search history.

(56) References Cited

U.S. PATENT DOCUMENTS

2014/0305810 A1    10/2014    Pontus von Bahr et al.
2017/0065208 A1*    3/2017    Furusaki ............ G01N 27/4067

FOREIGN PATENT DOCUMENTS

| ES | 2296917 T3 | 5/2008 | |
|---|---|---|---|
| WO | 2010094967 A1 | 8/2010 | |
| WO | 2011104567 A1 | 9/2011 | |
| WO | 2012059835 A1 | 5/2012 | |
| WO | WO-2012059835 A1 * | 5/2012 | ........... G01N 33/497 |
| WO | WO-2012160214 A1 * | 11/2012 | ........... G01N 33/497 |

OTHER PUBLICATIONS

WO 2012160214 A1-English (Year: 2014).*
WO 2012059835 A1-English (Year: 2012).*
International Search Report dated Jul. 13, 2017 for PCT/ES2017/070327 and English translation.

* cited by examiner

DEVICE FOR MEASURING THE CONCENTRATION OF GASES IN EXHALED AIR AND MEASUREMENT PROCEDURE USED

CROSS REFERENCE TO RELATED APPLICATION

This Application is a 371 of PCT/ES2017/070327 filed on May 17, 2017 which, in turn, claimed the priority of Spanish Patent Application No. 201630690 filed on May 27, 2016, both applications are incorporated herein by reference.

FIELD OF THE ART

The present invention relates to the analysis of the concentration of gases in the exhaled air of a human being, and particularly to a device and a procedure for measuring the concentration of nitric oxide (NO) in the air exhaled by a patient which is independent of the concentration of nitric oxide in the ambient air.

STATE OF THE ART

The analysis of exhaled air is a non-invasive technique whereby a picture of the blood composition can be obtained, which allows obtaining conclusive diagnoses concerning different aspects of the patient, mainly in relation to the prediction and control of asthma, although it can also be applied to the detection of lactose intolerance or other conditions.

Specifically, the determination of nitric oxide in exhaled air (FE NO) is a non-invasive technique which provides information about the eosinophilic inflammation of the airways, in connection with the disease of asthma, which is standardized by American Thoracic Society (ATS) and the European Respiratory Society (ERS) for the treatment of asthmatic patients.

The concentration of nitric oxide can be measured with an air analyzer which allows detecting an increase in the concentration of nitric oxide in the air exhaled by the patient and determining, depending on the increase in the concentration of nitric oxide, if there is any condition affecting the airways.

Patent document ES2221596T3 discloses equipment for analyzing exhaled air, comprising a first air inlet with a nozzle through which the patient exhales air into an air accumulation compartment, a second air inlet with a nitric oxide filter for introducing filtered ambient air in the equipment, a suction pump for suctioning ambient air into the equipment, valves for controlling the circulation of air through the inside of the equipment, and a sensor which measures the concentration of nitric oxide in the air exhaled by the patient.

In order to take the measurement of the nitric oxide, there is a first phase in which an initial venting of the equipment is performed collecting filtered ambient air from the outside by means of the pump through the second air inlet having the nitric oxide filter; in a second phase, using the equipment, the patient inhales air filtered by the nitric oxide filter through the nozzle of the first air inlet; and in a third phase, the patient exhales the air into the accumulation compartment. Once the air has accumulated in the compartment, the pump starts operating so as to extract a constant air flow on the nitric oxide sensor, and the concentration of nitric oxide in the air exhaled by the patient is determined.

The fact that the patient has to inhale air from the inside of the equipment means that it is an uncomfortable process, which results in an important constraint taking into account that the equipment is mainly to be used by asthmatic patients. Likewise, inhaling air from the inside of the equipment also results in a rather unhygienic process. On the other hand, the measurement procedure is slow, since the user must wait for the air accumulation compartment to be discharged in order to learn the result of the measurement.

Analyzers that do not require the patient to inhale air using the equipment are known (such as patent documents ES2296917T3 and WO2010094967A1, for example). With this equipment, the patient usually inhales ambient air and then exhales the air into the equipment, where the air is not stored, but rather passes directly through the nitric oxide sensor.

Analyzers of this type work correctly when the levels of the concentration of nitric oxide in the environment are low or nil. However, when these levels are high, measurements are negatively affected, since the patient may inhale air that is contaminated with nitric oxide.

The levels of nitric oxide in the environment have been found to vary significantly under uncontrollable conditions such as changes in humidity and temperature, the time of year, and atmospheric contamination. Likewise, inside buildings, there may also be changes depending on ventilation, other gases, and therefore contaminants that may exist, room occupation, or other factors. This fact is particularly important when using exhaled air analyzers, since they constitute portable equipment used in hospital settings.

See for example "Marczin, N., Kharitonov, S., Yacoub, M., Barnes, P. (2003), *"Disease markers in exhaled breath"*; Imperial College of Science, Technology and Medicine; National Heart and Lung Institute; London", which shows references to factors affecting the concentration of nitric oxide in exhaled air, as in the case of environmental pollution, the formation of nitric oxide in different cavities of the human body (so as to justify the need to measure different airflows), and the interpretation of cross-measurements between nitric oxide and carbon monoxide as markers of different diseases.

Also see "Boeker, P., Wallenfang, O., Horner, G., *Mechanistic model of diffusion and reaction in thin sensor layers—the DIRMAS model; Sensors and Actuators B* 83 (2002) 202-208", which shows a mathematical model for solving the problem of the cumulative effect on sensors.

An exhaled air analyzer that can take reliable, quick, and repetitive measurements that are independent of the nitric oxide present in the environment in which the measurement is taken and which can be used in an easy and comfortable manner by the patients, has therefore become necessary.

OBJECT OF THE INVENTION

The object of the present invention is to provide a measurement device and procedure, whereby enabling the evaluation of the concentration of nitric oxide in the air exhaled by a person in a more reliable and simple manner.

The device for measuring the concentration of gases in exhaled air of the invention comprises:
- a first air inlet for introducing unfiltered ambient air and air exhaled by a patient in the device,
- a second air inlet with a nitric oxide filter for introducing filtered ambient air in the device,
- a pump for suctioning ambient air into the device,
- a nitric oxide sensor for measuring the concentration of nitric oxide in the air, a first valve located downstream from the first air inlet and upstream from the nitric oxide sensor, and a second valve located downstream from the second air inlet and upstream from the nitric oxide sensor, a third valve located downstream from the nitric oxide sensor in a first fluid line that conducts the air exhaled by the patient to a first air outlet, and a fourth valve located downstream from the nitric oxide sensor in a second fluid line that conducts the ambient air to a second air outlet, and wherein the pump for suctioning ambient air is located in the second fluid line.

The measurement device does not have a compartment for storing the air exhaled by the patient as the devices of the state of the art do, such that the measurement of the concentration of nitric oxide is taken directly in the moment in which the patient blows into the first air inlet, whereby the results of the measurement can be obtained about 5 seconds after finishing the exhalation of air. Directly taking the measurement is also advantageous so that the device can be used by children, since with them it is necessary to take several measurements in a row with a short time interval between measurements.

On the other hand, the arrangement of the first and second valves upstream from the nitric oxide sensor allows closing the air passage established with the first and second air inlets, and the arrangement of the third and fourth valves downstream from the nitric oxide sensor allows closing the air passage established with the outside of the device, such that the four valves allow isolating the nitric oxide sensor during the measurement, such that the nitric oxide measurements are taken with the sensor in a leak-tight mode, which allows stabilizing nitric oxide curve obtained by the sensor and thereby improving its measurement efficacy.

Downstream from the first air inlet there are arranged a pressure sensor and a flow meter for measuring the pressure and the flow rate of the air exhaled by the patient, these measurements being depicted on a display which allows the patient to maintain the exhalation flow within the ranges put forth by the American Thoracic Society (ATS) and the European Respiratory Society (ERS).

Upstream from the nitric oxide sensor there is arranged a humidity stabilizer for stabilizing the humidity of the ambient air and the humidity of the air exhaled by the patient before it goes through the nitric oxide sensor.

Downstream from the first air inlet there is arranged an air exhaust to reduce the air pressure inside the device and so that the patient does not feel excessive pressure in the mouth during the exhalation of the air.

The measurement procedure for measuring the concentration of gases in exhaled air of the invention comprises the following stages:

taking a first measurement M1 of the concentration of nitric oxide in the filtered ambient air by taking ambient air through the second air inlet with a nitric oxide filter, taking a second measurement M2 of the concentration of nitric oxide in the unfiltered ambient air by taking ambient air through the first air inlet, taking a third measurement M3 of the concentration of nitric oxide in the filtered ambient air by taking ambient air through the second air inlet with a nitric oxide filter, taking a fourth measurement M4 of the concentration of nitric oxide in the air exhaled by a patient through the first air inlet, and calculating the concentration of nitric oxide in the air exhaled by the patient according to the following equation:

[concentration of nitric oxide=$(M4-M3)-(M2-M1)$]

According to said procedure, the precision and repeatability of the measurements under changing conditions of the concentration of nitric oxide in the environment can be improved, since in order to take the measurements the concentration of nitric oxide in the environment where the test is being performed is taken under consideration. Furthermore, the first measurement M1 and third measurement M3 allow cleaning the air circulation pathways inside the device which have been in contact with the nitric oxide of the unfiltered ambient air or of the exhaled air, leaving the device prepared so that the next measurement is not contaminated. On the other hand, the nitric oxide sensor must take the measurement in short time periods, so the recovery time periods of the sensor are barely respected, where pseudo-drifts affecting the measurement may even occur. It has experimentally been observed that said first measurement M1 and third measurement M3 allow correcting these pseudo-drifts, obtaining more precise measurement values of nitric oxide.

The second measurement and the fourth measurement M4 of the concentration of nitric oxide in the air exhaled by the patient are taken with the first valve, second valve, third valve, and fourth valve closed, with the nitric oxide sensor being in a leak-tight state while taking the measurement to enable stabilizing the response curve of the sensor, and to thereby enable assuring a suitable measurement of the concentration of nitric oxide.

The procedure additionally comprises at least one cleaning stage which can take place before taking the first measurement or after taking any of the measurements. The cleaning stage has a first step in which the air pathway established between the second air inlet and the second air outlet is cleaned, a second step in which the air pathway established between the first air inlet and the second air outlet is cleaned, and a third step in which the air pathway established between the second air inlet and the second air outlet is cleaned again.

Therefore, a device is obtained, whereby measurements of the nitric oxide present in the air exhaled by a patient can be taken in a reliable, quick, and repeatable manner, without inconveniencing the patient using the device since it does not require the inhalation of the air through the device, in a quicker manner than with devices of the state of the art since this one does not require storage of the exhaled air, and in which the obtained measurements are independent of the nitric oxide present in the environment in which the measurement is taken.

DETAILED DESCRIPTION OF THE INVENTION

In the sense of the present invention, in relation to a section of the course of the air through the inside of the device, it is understood that a point is downstream if it is located after the considered section, advancing in the direction of the air stream, and it is understood that a point is upstream if it is located after the considered section, advancing in the direction opposite to the air stream. The direction of the air stream through the inside of the device is depicted by means of a dotted line in FIGS. 2 to 4.

Figure 1:
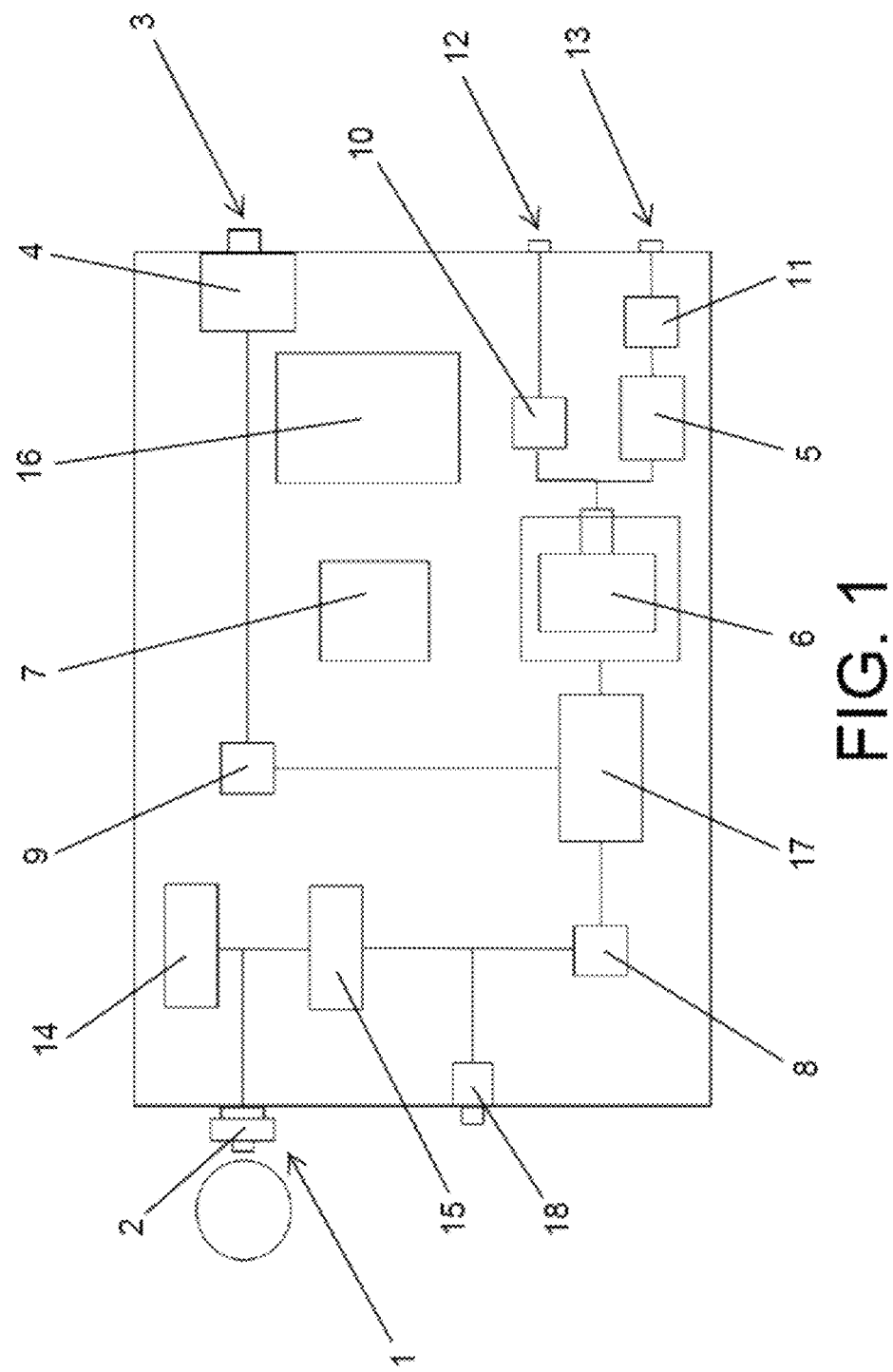
FIG. 1 shows a schematic view of the device for measuring the concentration of gases in exhaled air of the invention.

FIG. 1 shows a schematic view of the device for measuring the concentration of gases in exhaled air of the invention. The device comprises a first air inlet (1) having a nozzle (2) provided with an antibacterial filter through which the patient exhales air into the device and through which unfiltered ambient air is also introduced into the device, a second air inlet (3) with a nitric oxide filter (4) through which ambient air in which nitric oxide has been filtered out is introduced, a pump (5) whereby ambient air, both filtered and unfiltered, is forced to enter the device, a nitric oxide sensor (6) for measuring the concentration of nitric oxide, and a control unit (7) which controls the opening and closing of valves (8, 9, 10, 11) which control the passage of the air through the inside of the device.

The control unit (7) has an internal memory in which data from the measurements taken with the nitric oxide sensor (6) can be stored, and said measurements can be exported to an external file for subsequent processing. Likewise, the control unit (7) has communication means for remotely managing the data obtained from the measurements, such as for example USB- type communication means, or wireless communication means, such as Bluetooth, ZigBee, or the like. The device comprises a first valve (8) located downstream from the first air inlet (1) and upstream from the nitric oxide sensor (6), a second valve (9) located downstream from the second air inlet (3) and upstream from the nitric oxide sensor (6), a third valve (10) located downstream from the nitric oxide sensor (6) in a first fluid line connecting with a first air outlet (12), and a fourth valve (11) located downstream from the nitric oxide sensor (6) in a second fluid line connecting with a second air outlet (13). The pump (5) is located in the second fluid line, preferably upstream from the fourth valve (11).

The valves (8, 9, 10, 11) are electrically-operated valves which can switch between a state that allows the passage of fluid therethrough and a state which blocks the passage, although the first and second valves (8, 9) may be an electrically-operated three-way valve, which can switch between a state which allows communicating the first air inlet (1) to the nitric oxide sensor (6), or a state which allows communicating the second air inlet (3) to the nitric oxide sensor (6).

Downstream from the first air inlet (1) there are arranged a pressure sensor (14) and a flow meter (15) which determine the pressure and the flow rate of the air exhaled by the patient, said information being used to determine the concentration of nitric oxide in the exhaled air. The information about the pressure and the flow rate of the air exhaled by the patient is depicted on a display (16) in order for the patient to keep the exhalation pressure within recommended limits (5-20 cm $H_2O$) for obtaining the measurement. The information about the flow rate can be digitally depicted on the display (16), or an analog flow meter (15) provided with a needle indicating the flow rate of the air which is being exhaled by the patient can be used.

Upstream from the nitric oxide sensor (6) and downstream from the first valve (8) and second valve (9) there is arranged a humidity stabilizer (17) which allows stabilizing both the humidity of the ambient air and the humidity of the air exhaled by the patient.

Downstream from the first air inlet (1), and preferably downstream from the flow meter (15) and upstream from the first valve (8), there is arranged an air exhaust (18) which reduces the air pressure inside the device, such that the patient does not have to make a major effort in the exhalation, due to the increase in pressure in the mouth. It is therefore the patient himself or herself who can control the exhaled air flow according to limits established for measuring nitric oxide by modulating the exhalation depending on the air flow rate indicated on the display (16). The air exhaust (18) can be an electrically-operated valve or a fixed valve, or any other type of exhaust valve which allows throttling the air to reduce the pressure exerted by the user.

Figure 2:
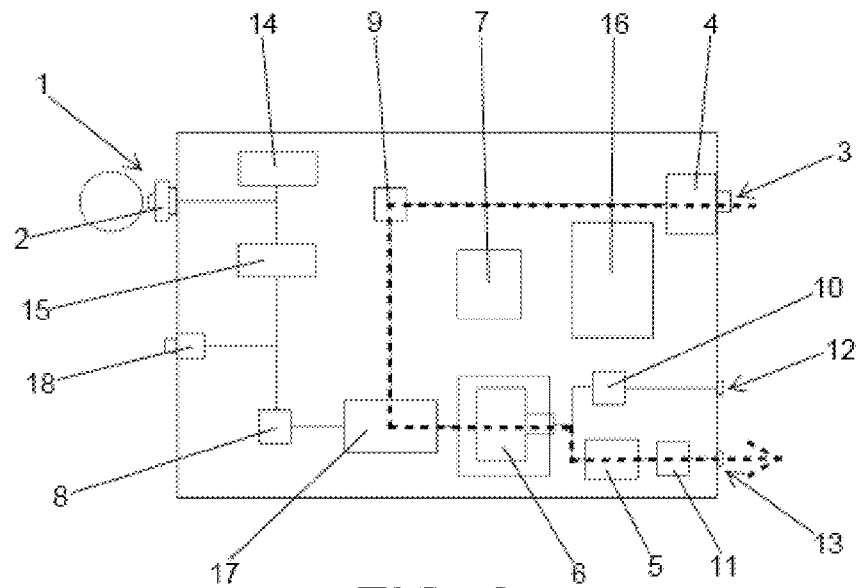
FIG. 2 shows a stage of the procedure of the invention in which a measurement of the concentration of nitric oxide in the ambient air is taken through the nitric oxide filter of the device.

Therefore, the measurement procedure for measuring the concentration of gases of the invention has a first stage, depicted in FIG. 2, in which a first measurement (M1) of the concentration of nitric oxide in the filtered ambient air on which the test is performed is taken, such that an initial reference point is established for the measurement of the concentration of nitric oxide in the unfiltered ambient air which will be taken in a second stage. To that end, the pump (5) is activated while the first valve (8) and the third valve (10) are closed and the second valve (9) and fourth valve (11) are open, such that ambient air filtered by the nitric oxide filter (4) is taken, making it go through the nitric oxide sensor (6), and it exits the device through the second air outlet (13) of the second fluid line.

Figure 3:
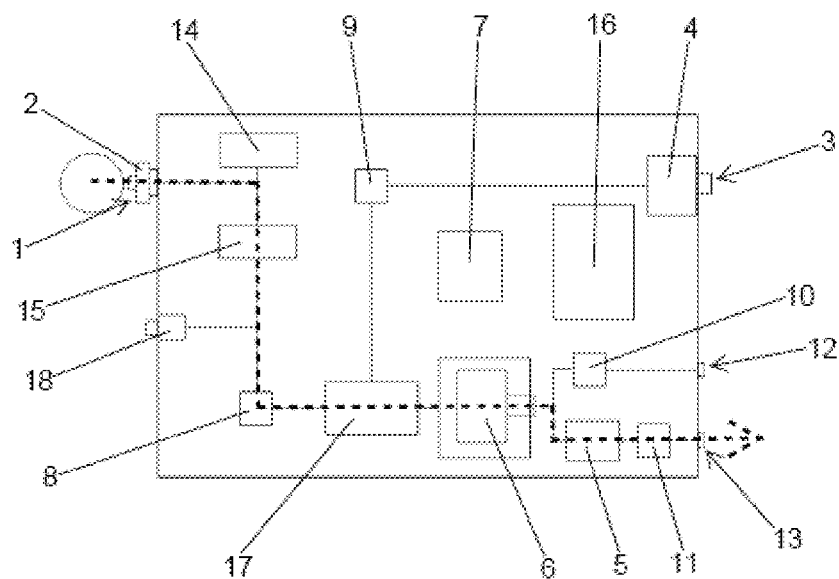
FIG. 3 shows another stage of the procedure of the invention in which a measurement of the concentration of nitric oxide in the ambient air is taken through the nozzle of the device.

In the second stage, depicted in FIG. 3, a second measurement (M2) of the concentration of nitric oxide in the unfiltered ambient air is taken, such that the concentration of nitric oxide in the ambient air on which the test will be conducted is measured directly. The second stage has a first sub-stage in which the pump (5) is activated while the second valve (9) and third valve (10) are closed and the first valve (8) and fourth valve (11) are open, such that unfiltered ambient air is taken through the nozzle (2) of the first air inlet (1), making it go through the nitric oxide sensor (6), and it exits the device through the second air outlet (13) of the second fluid line. Next, there is a second sub-stage in which the pump (5) is deactivated and all the valves (8, 9, 10, 11) are closed, such that the measurement of the nitric oxide is taken with the nitric oxide sensor (6) in a leak-tight mode, which allows stabilizing the nitric oxide curve obtained by the sensor (6).

The pump (5) therefore collects unfiltered ambient air for about 10 seconds at a flow of about 3 l/min and, in about the next 5 seconds the valves (8, 9, 10, 11) are closed to stabilize the response curve of the nitric oxide sensor (6), and the measurement of the concentration of nitric oxide is taken during the time interval in which the valves (8, 9, 10, 11) are closed.

In a third stage, likewise depicted in FIG. 2, a third measurement (M3) of the concentration of nitric oxide in filtered ambient air is taken, with another initial reference point being established for the measurement of the concentration of nitric oxide in the air exhaled by the patient which will be performed in a fourth stage. The procedure is identical to that of the first stage, the pump (5) is activated while the first valve (8) and the third valve (10) are closed and the second valve (9) and the fourth valve (11) are open, by taking ambient air filtered by the nitric oxide filter (4), making it go through the nitric oxide sensor (6), and the air exiting the device through the second air outlet (13) of the second fluid line.

Figure 4:
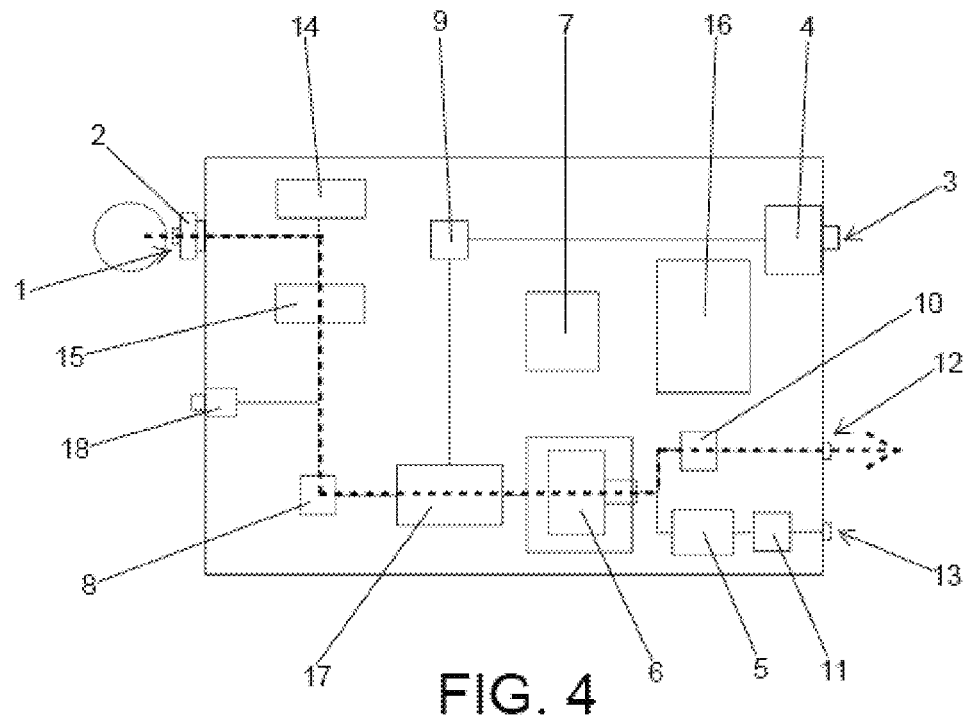
FIG. 4 shows another stage of the procedure of the invention in which a measurement of the concentration of nitric oxide in the air exhaled by the patient is taken through the nozzle of the device.
Figure 5:
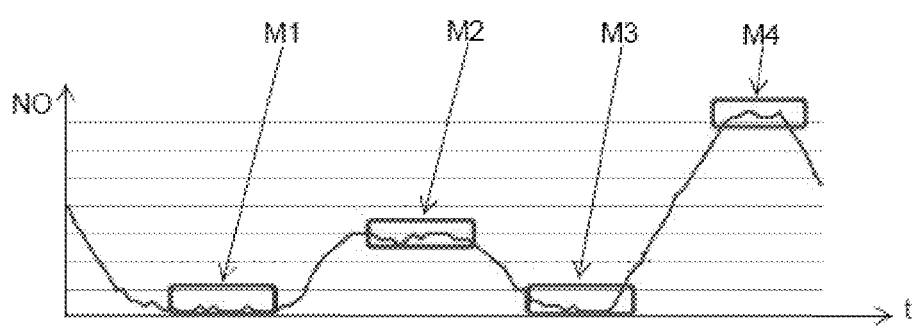
FIG. 5 shows the response curve obtained by the nitric oxide sensor by applying the procedure of the invention.

In the fourth stage depicted in FIG. 4, a fourth measurement (M4) of the concentration of nitric oxide in the air exhaled by the patient is taken through the first air inlet (1). The fourth stage has a first sub-stage in which the second valve (9) and the fourth valve (11) are closed and the first valve (8) and the third valve (10) are open, such that the patient exhales air through the nozzle (2) of the first air inlet (1), which goes through the nitric oxide sensor (6) and exits the device through the first air outlet (12) of the first fluid line. Next, there is a second sub-stage in which all the valves (8, 9, 10, 11) are closed, such that the measurement of nitric oxide is taken with the nitric oxide sensor (6) in a leak-tight mode to achieve stabilization of the curve obtained by the nitric oxide sensor (6).

In this sense, the user thereby usually inhales ambient air from the environment in which he or she is located, and next exhales through the nozzle (2) maintaining a constant flow of about 3 l/min for about 10 seconds, for which he or she is aided by the information about the pressure sensor (14) and about the flow meter (15) depicted on the display (16). During the exhalation of the first sub-stage, the nitric oxide sensor (6) begins to establish the profile of the response curve that is obtained depending on the contribution of nitric oxide by the patient. Once exhalation has ended, in the second sub-stage, the nitric oxide sensor (6) is in a leak-tight mode, with all the valves (8, 9, 10, 11) being closed for about 5 seconds to stabilize the response curve of the nitric oxide sensor (6) and to enable taking measurements of the concentration of nitric oxide during said time interval.

A summary table is shown below with the opening and closing state of the valves (8, 9, 10, 11), as well as the activation and deactivation state of the pump (5), during the four stages of the procedure of the invention:

| Stage | First valve | Second valve | Third valve | Fourth valve | Pump |
|---|---|---|---|---|---|
| Stage 1 | Closed | Open | Closed | Open | Active |
| Stage 2; First sub-stage | Open | Closed | Closed | Open | Active |
| Stage 2; Second sub-stage | Closed | Closed | Closed | Closed | Inactive |
| Stage 3 | Closed | Open | Closed | Open | Active |
| Stage 4; First sub-stage | Open | Closed | Open | Closed | Inactive |
| Stage 4; Second sub-stage | Closed | Closed | Closed | Closed | Inactive |

With the values of the four measurements (M1, M2, M3, M4) obtained by the nitric oxide sensor (6), the concentration of nitric oxide in the air exhaled by the patient is calculated, taking into account for said calculation the concentration of nitric oxide in the ambient air in which the device is located. To that end, the calculation is performed according to the following equation:

[concentration of nitric oxide=(*M4*−*M3*)−(*M2*−*M1*)]

The measurement (M4) of the concentration of nitric oxide in the air exhaled by the patient is thereby compared with the measurement (M2) of the concentration of nitric oxide in ambient air from where the patient inhales the air. Likewise, the concentration of nitric oxide in the air exhaled by the patient and the concentration of nitric oxide in ambient air are respectively compared with a reference measurement (M1, M3) of the ambient air filtered by the nitric oxide filter (6), whereby assuring the precision and repeatability in the measurements taken regardless of the variability of the concentration of nitric oxide existing in the ambient air in which the patient is located, which is particularly relevant for portable devices used in hospital settings, as in the case of the present invention.

It is evident for one skilled in the art that the third and fourth stages can be carried out before the first and second stages, without this alteration of the stages of the procedure altering the object of the invention.

It has experimentally been found that a direct comparison of the fourth and second measurements (M4) and (M2) does not allow precise and repeatable measurements, which is essential in devices of this type. This is because the device must take measurements of low concentrations of nitric oxide in a very short time span, so response and recovery times of the sensor (6) are minimized, and as a result the recovery time of the sensor (6) is not respected, where pseudo-drifts in the measurement curve of the sensor (6) may occur as described in "Boeker, P., Wallenfang, O., Horner, G., *Mechanistic model of diffusion and reaction in thin sensor layers—the DIRMAS model; Sensors and Actuators B* 83 (2002) 202-20 208". When taking the first and third measurements (M1) and (M3), that pseudo-drift in the value measured by the sensor (6) can be corrected and a more precise value obtained.

Additionally, before taking the first measurement (M1), or after taking each of the measurements (M1, M2, M3, M4), a cleaning stage for cleaning the air circulation pathways to eliminate possible leftover air from a previous use, can be performed. It has been envisaged that the cleaning stage comprises a first step of about 10 seconds in which the air pathway established between the second air inlet (3) and the second air outlet (13) is cleaned, for which purpose the first valve (8) and the third valve (10) are closed and the second valve (9) and the fourth valve (11) are open, a second step of about 40 seconds in which the air pathway established between the first air inlet (1) and the second air outlet (13) is cleaned, for which the second valve (9) and third valve (10) are closed and the first valve (8) and fourth valve (11) are open, and a third step of about 10 seconds in which the air pathway established between the second air inlet (3) and the second air outlet (13) is cleaned again, for which the first valve (8) and the third valve (10) are closed and the second valve (9) and the fourth valve (11) are open.

A summary table is shown below with the opening and closing state of the valves (8, 9, 10, 11), as well as the activation and deactivation state of the pump (5) during the three steps of a cleaning stage.

| Step | First valve | Second valve | Third valve | Fourth valve | Pump |
|---|---|---|---|---|---|
| First step | Closed | Open | Closed | Open | Active |
| Second step | Open | Closed | Closed | Open | Active |
| Third step | Closed | Open | Closed | Open | Active |

Nitric oxide is known to be produced along the entire tracheobronchial tree, the nitric oxide coming from alveoli (Calv,NO) and the nitric oxide synthesized in the more central airways (Dalv,NO) being different from one another. The exhalation flow provided by the patient is what allows determining what type of nitric oxide contributes to a greater extent to the final result of the nitric oxide measured by the sensor. In order to obtain measurements of the different types of nitric oxide, the patient must exhale air at different flows, such as 3 l/min, 6 l/m, and 9 l/m, for example, for which the patient receives the aid of information about the pressure sensor (14) and flow meter (15) depicted on the display (16).

To reduce the air pressure that may be produced inside the device due to the different exhalation flows, and so that the patient does not have to make a major effort in the exhalation due to an increase in pressure in the mouth, according to an embodiment of the invention, there arrangement of three air exhausts downstream from the first air inlet (1) conducting part of the exhaled air to the outside, and each of which is configured for throttling the air according to a given flow rate in connection with the different exhalation flows of the patient, have been envisaged. For example, a first air exhaust throttling the air at a flow rate of 1.5 l/min when the exhalation flow is 3 l/min, a second air exhaust throttling the air at a flow rate of 4.5 l/min when the exhalation flow is 6 l/min, and a third air exhaust throttling the air at a flow rate of 7.5 l/min when the exhalation flow is 9 l/min.

According to another embodiment of the invention, the measurement device additionally comprises other sensors for detecting gases other than a nitric oxide sensor (6) to, on one hand, measure the cross-correlations of gases interfering in the sensors, and on the other hand, take those measurements as indicators of the root of the problem of different diseases. In that sense, this device may additionally comprise a carbon monoxide sensor for measuring the concentration of carbon monoxide in the air, and/or a hydrogen sensor for measuring the concentration of hydrogen in the air, these additional sensors being arranged in air pathways parallel to the air pathway of the nitric oxide sensor (6).

The invention claimed is:

1. A device for measuring the concentration of gases in exhaled air, comprising:
    a first air inlet for introducing unfiltered ambient air and air exhaled by a patient in the device,
    a second air inlet with a nitric oxide filter for introducing filtered ambient air in the device,
    a pump for suctioning ambient air into the device, a nitric oxide sensor for measuring the concentration of nitric oxide in the air,
    a first valve located downstream from the first air inlet and upstream from the nitric oxide sensor,
    a second valve located downstream from the second air inlet and upstream from the nitric oxide sensor,
    a third valve located downstream from the nitric oxide sensor in a first fluid line that conducts the air exhaled by the patient to a first air outlet, and
    a fourth valve located downstream from the nitric oxide sensor in a second fluid line that conducts the ambient air to a second air outlet, and wherein the pump for suctioning ambient air is located in the second fluid line.

2. The device for measuring the concentration of gases in exhaled air according to claim 1, wherein downstream from the first air inlet there are arranged a pressure sensor and a flow meter for measuring the pressure and the flow rate of the air exhaled by the patient.

3. The device for measuring the concentration of gases in exhaled air according to claim 1, wherein upstream from the nitric oxide sensor there is arranged a humidity stabilizer.

4. The device for measuring the concentration of gases in exhaled air according to claim 1, wherein downstream from the first air inlet there is arranged at least one air exhaust to reduce the air pressure inside the device.

5. The device for measuring the concentration of gases in exhaled air according to claim 4, wherein downstream from the first air inlet there are arranged three air exhausts, each of which is configured for throttling the air according to a given flow rate which is a function of the air exhaled by the patient.

6. The device for measuring the concentration of gases in exhaled air according to claim 1, further comprising a carbon monoxide sensor for measuring the concentration of carbon monoxide in the air.

7. A measurement procedure for measuring the concentration of gases in exhaled air which uses a device defined according to claim 1, comprising the stages of:
    taking a first measurement of the concentration of nitric oxide in the filtered ambient air by taking ambient air through the second air inlet with a nitric oxide filter,
    taking a second measurement of the concentration of nitric oxide in the unfiltered ambient air by taking ambient air through the first air inlet,
    taking a third measurement of the concentration of nitric oxide in the filtered ambient air by taking ambient air through the second air inlet with a nitric oxide filter,
    taking a fourth measurement of the concentration of nitric oxide in the air exhaled by a patient through the first air inlet, and
    calculating the concentration of nitric oxide in the air exhaled by the patient according to the following equation:

$$[\text{concentration of nitric oxide}=(M4-M3)-(M2-M1)].$$

8. The measurement procedure for measuring the concentration of gases in exhaled air according to claim 7, wherein the fourth measurement of the concentration of nitric oxide in the air exhaled by the patient is taken with the first valve, second valve, third valve, and fourth valve closed, with the nitric oxide sensor being in a leak-tight state while taking the fourth measurement.

9. The measurement procedure for measuring the concentration of gases in exhaled air according to claim 7, wherein the second measurement of the concentration of nitric oxide in the unfiltered ambient air is taken with the first valve, second valve, third valve, and fourth valve closed, with the nitric oxide sensor being in a leak-tight state while taking the second measurement.

10. The measurement procedure for measuring the concentration of gases in exhaled air according to claim 7, wherein when taking the first measurement or the third measurement, the pump is activated while the first valve and the third valve are closed and the second valve and the fourth valve are open.

11. The measurement procedure for measuring the concentration of gases in exhaled air according to claim 7, wherein when taking the second measurement there is a first sub-stage in which the pump is activated while the second valve and third valve are closed and the first valve and fourth valve are open, and a second sub-stage in which the pump is deactivated and all the valves, are closed, with the nitric oxide sensor being in a leak-tight state while taking the second measurement.

12. The measurement procedure for measuring the concentration of gases in exhaled air according to claim 7, wherein when taking the fourth measurement there is a first sub-stage in which the second valve and the fourth valve are closed and the first valve and the third valve are open, and a second sub-stage in which all the valves are closed, with the nitric oxide sensor being in a leak-tight state while taking the second measurement.

13. The measurement procedure for measuring the concentration of gases in exhaled air according to claim 7, wherein the procedure additionally comprises at least one cleaning stage having a first step in which the air pathway established between the second air inlet and the second air outlet is cleaned, a second step in which the air pathway established between the first air inlet and the second air outlet is cleaned, and a third step in which the air pathway established between the second air inlet and the second air outlet is cleaned again.

* * * * *